US012773180B2

(12) United States Patent
Reymann et al.

(10) Patent No.: US 12,773,180 B2
(45) Date of Patent: Oct. 27, 2026

(54) AUTOMATED CALIBRATION OF MOBILE IMAGING SYSTEMS

(71) Applicant: Siemens Medical Solutions USA, Inc., Malvern, PA (US)

(72) Inventors: Maximilian Reymann, Erlangen (DE); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 159 days.

(21) Appl. No.: 18/820,576

(22) Filed: Aug. 30, 2024

(65) Prior Publication Data

US 2026/0063813 A1 Mar. 5, 2026

(51) Int. Cl.

| | |
|---|---|
| ***A61B 6/03*** | (2006.01) |
| ***A61B 6/00*** | (2006.01) |
| ***A61B 6/42*** | (2024.01) |
| ***A61B 6/58*** | (2024.01) |
| ***G01T 1/164*** | (2006.01) |
| ***G01T 1/24*** | (2006.01) |
| ***G01T 1/29*** | (2006.01) |
| ***G01T 7/00*** | (2006.01) |

(52) U.S. Cl.

CPC .............. *A61B 6/585* (2013.01); *A61B 6/035* (2013.01); *A61B 6/037* (2013.01); *A61B 6/4258* (2013.01); *A61B 6/4405* (2013.01); *A61B 6/56* (2013.01); *A61B 6/566* (2013.01); *A61B 6/582* (2013.01); *G01T 1/1642* (2013.01); *G01T 1/1648* (2013.01); *G01T 1/249* (2013.01); *G01T 1/2985* (2013.01); *G01T 7/005* (2013.01)

(58) Field of Classification Search

CPC ........... A61B 6/03; A61B 6/032; A61B 6/035; A61B 6/037; A61B 6/42; A61B 6/4208; A61B 6/4241; A61B 6/4258; A61B 6/4266; A61B 6/4275; A61B 6/44; A61B 6/4405; A61B 6/56; A61B 6/566; A61B 6/582; A61B 6/585; G01T 1/1642; G01T 1/1648; G01T 1/249; G01T 1/2985

USPC ................ 378/19, 101, 102, 207; 250/252.1, 250/363.01, 363.02, 363.03, 363.04, 250/363.05, 363.07, 363.08, 363.09

See application file for complete search history.

(56) References Cited

U.S. PATENT DOCUMENTS

| | | | | |
|---|---|---|---|---|
| 7,026,622 B2 * | 4/2006 | Kojima | .................. | A61B 6/037 250/363.04 |
| 7,247,844 B2 * | 7/2007 | Thompson | ............. | A61B 6/037 250/363.03 |

(Continued)

FOREIGN PATENT DOCUMENTS

| | | |
|---|---|---|
| WO | 2019025770 | 2/2019 |
| WO | 2021211941 | 10/2021 |

OTHER PUBLICATIONS

Vohradsky J et al: "Introduction and implementation of the CMRP radiodosimeter—a novel wireless microdosimetry system", Mar. 7, 2022, vol. 17, No. 3, Mar. 7, 2022 (Mar. 7, 2022).

*Primary Examiner* — Allen C. Ho

(57) ABSTRACT

A framework for automated calibration of mobile imaging systems. A mobile imaging system is positioned at a station. Detection of emissions from a calibration source at the station by the mobile imaging system is initiated to generate emission data. Calibration of the mobile imaging system may then be performed using the emission data.

20 Claims, 4 Drawing Sheets

(56) References Cited

U.S. PATENT DOCUMENTS

| | | | | |
|---|---|---|---|---|
| 7,297,958 | B2 * | 11/2007 | Kojima | A61B 6/037<br>250/363.04 |
| 7,519,156 | B2 * | 4/2009 | Marar | A61B 6/4494<br>378/207 |
| 7,872,221 | B2 * | 1/2011 | Blevis | G01T 1/249<br>250/252.1 |
| 8,000,773 | B2 * | 8/2011 | Rousso | A61B 6/583<br>250/370.08 |
| 8,325,875 | B2 * | 12/2012 | Omernick | A61B 6/563<br>378/62 |
| 8,384,015 | B2 * | 2/2013 | Blevis | A61B 6/4258<br>250/493.1 |
| 8,415,632 | B2 * | 4/2013 | Tsukerman | G01T 1/1647<br>250/363.09 |
| 8,785,869 | B2 * | 7/2014 | McParland | A61B 6/4258<br>378/37 |
| 9,289,184 | B2 * | 3/2016 | Lalena | A61B 6/585 |
| 9,504,431 | B2 * | 11/2016 | Bhattacharya | A61B 6/582 |
| 10,463,252 | B2 | 11/2019 | Sanpitak | |
| 10,568,602 | B2 * | 2/2020 | Tkaczyk | A61B 6/584 |
| 11,284,847 | B2 * | 3/2022 | Minnigh | A61B 6/4035 |
| 11,497,461 | B1 * | 11/2022 | Vija | A61B 6/037 |
| 12,170,153 | B2 * | 12/2024 | Nunn | A61B 6/582 |

* cited by examiner

AUTOMATED CALIBRATION OF MOBILE IMAGING SYSTEMS

TECHNICAL FIELD

The present disclosure generally relates to medical imaging, and more particularly to automated calibration of mobile imaging systems.

BACKGROUND

Functional imaging uses a radioisotope or radiotracer to determine metabolic function within a patient. For example, the uptake of the radiotracer by tissues in the body is measured. Positron emission tomography (PET) and single photon emission computed tomography (SPECT) are two types of functional imaging. The emissions from the radiotracer are detected in the functional imaging. The activity concentration (i.e., the concentration of the radiotracer from different locations) is reconstructed from the detected emissions.

Typically, only one imaging system is assigned to one imaging suite for imaging one patient at a time. Injection of the patient occurs in the injection room, and the patient needs to go to the imaging suite thereafter. The patient may be ambulated or transported to the imaging suite, imaged and either released or transferred back to the station. This imaging process is performed for each imaging modality. It is a costly logistical problem as patients must be scheduled and transported from station or waiting/dressing room to imaging room with specially trained staff, since the patient is radioactive after the injection.

To ensure proper operation, the imaging system needs to shut down periodically to be calibrated or to perform other maintenance tasks. Such service occurs on the imaging system, which is fixedly mounted in the imaging room. The imaging room is typically the same room that is also occupied by the imaging patient, and is thus considered "patient space". It needs to be kept pleasant and safe at all times. If periodic maintenance or calibration occurs in the "patient" space and calibration equipment (e.g., calibration phantom, diagnostic system) brought to the imaging system, workflow is interrupted and efficiency is reduced as patients cannot occupy the space while maintenance or repair is performed.

SUMMARY

Described herein is a framework for automated calibration of mobile imaging systems. A mobile imaging system is positioned at a station. Detection of emissions from a calibration source at the station by the mobile imaging system is initiated to generate emission data. Calibration of the mobile imaging system may then be performed using the emission data.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
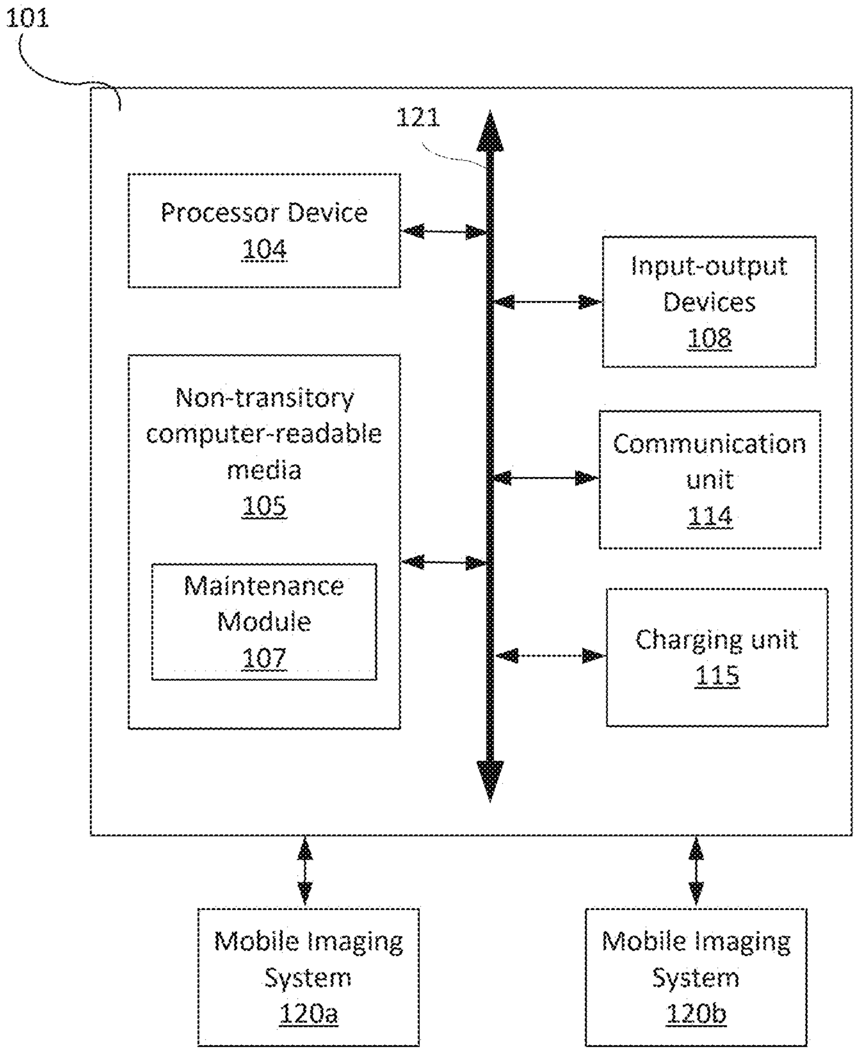
FIG. 1 is a block diagram illustrating an exemplary station.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

A framework for automated calibration of mobile medical imaging systems is presented herein. In accordance with one aspect, a station is provided to automatically calibrate and/or charge one or more mobile medical imaging systems. Such mobile imaging systems may move autonomously or semi-autonomously to the station. Alternatively, they may be manually moved to the station. One or more calibration sources may be positioned in a container at the station. Quality control (QC) may be performed during charging and/or calibration. A fleet of mobile imaging systems may be centrally managed. Mobile imaging systems that fail QC may be automatically flagged.

The framework advantageously provides automated calibration and/or charging of mobile imaging systems at a station. The framework optimizes management and maintenance of the mobile medical imaging device to ensure proper operation. Maintenance of the mobile medical imaging devices may include charging and calibration of one or more imaging detectors in the mobile medical imaging devices at docking stations for the mobile medical imaging devices. The calibration and/or charging of the mobile imaging system advantageously occur outside a "patient" space, such as within a storage area where the mobile imaging system is docked, thereby minimizing disruption to the workflow. These and other exemplary advantages and features will be described in more details in the following description.

FIG. 1 is a block diagram illustrating an exemplary station 101 for implementing the framework as described herein. In some implementations, station 101 operates as a standalone device. In other implementations, station 101 may be connected via communication unit 114 to other machines, such other stations 101. In a networked deployment, station 101 may operate as a peer machine in a peer-to-peer (or distributed) network environment. Any number of stations 101 may be provided (e.g., one, two, three or more) to serve one or more mobile imaging systems 120*a*-120*b*.

Station 101 may include a processor device or central processing unit (CPU) 104 coupled to one or more non-transitory computer-readable media 105 (e.g., computer storage or memory device), input-output devices 108 (e.g., monitor, mouse, touchpad or keyboard), communication unit 114 and charging unit 115 via an input-output interface 121. Station 101 may further include support circuits such as a cache, a power supply or battery, clock circuits and a communications bus (not shown). Station 101 may serve as, for example, a docking station for one or more mobile imaging systems 120*a*-120*b* in a storage location. Station 101 may provide charging and/or calibration services to mobile imaging systems 120*a*-120*b*. Various other peripheral devices, such as additional data storage devices and printing devices, may also be connected to the station 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in one or more non-transitory computer-readable media 105. In particular, the present techniques may be implemented by a maintenance module 107. Non-transitory computer-readable media 105 may include random access memory (RAM), read-only memory (ROM), magnetic floppy disk, flash memory, and other types of memories, or a combination thereof. The computer-readable program code is executed by processor device 104 to process data acquired by, for example, mobile imaging systems 120*a*-120*b*. The computer-readable program code is not intended to be limited to any particular programming language and implementation thereof. It will be appreciated that a variety of programming languages and coding thereof may be used to implement the teachings of the disclosure contained herein. The same or different computer-readable media 105 may be used for storing a database.

Communication unit 114 enables the station 101 to communicate with other stations, mobile imaging systems 120*a*-120*b* and/or other systems. Communication unit 114 may include wireless signal transceiver that communicate signals using a common communication protocol, such as Global System for Mobile Communications (GSM), WIFI, Bluetooth, Zigbee, LoRa, and TCP/IP. Other types of communication protocols are also useful. The wireless communications may be used to summon the mobile imaging systems 120*a*-120*b* to perform a maintenance task (e.g., charging, calibration).

Charging unit 115 supplies power to charge one or more batteries in mobile imaging systems 120*a*-120*b*. Wired and/or wireless charging may be provided. Charging unit 115 may receive input power from an external power source, such as a standard wall power outlet, and may include one or more charging pads and associated charging circuitry to supply power to the mobile imaging systems 120*a*-120*b*. Additional circuitry may be provided to condition the input power to render it suitable for recharging the battery. A single charging unit 115 may provide charging for multiple mobile imaging systems 120*a*-120*b*.

Each mobile imaging system (120*a*, 120*b*) acquires medical image data. Each mobile imaging system (120*a*, 120*b*) may be a tomographic scanner (e.g., nuclear medicine scanner) for acquiring, collecting and/or storing such medical image data. Each mobile imaging system (120*a*, 120*b*) may be a single-photon emission computed tomographic (SPECT), positron emission tomographic (PET), computed tomographic (CT) or other tomographic (e.g., ultrasound or surgical) imaging system. Diagnostic, theragnostic, dosimetry or surgical support imaging may be provided.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
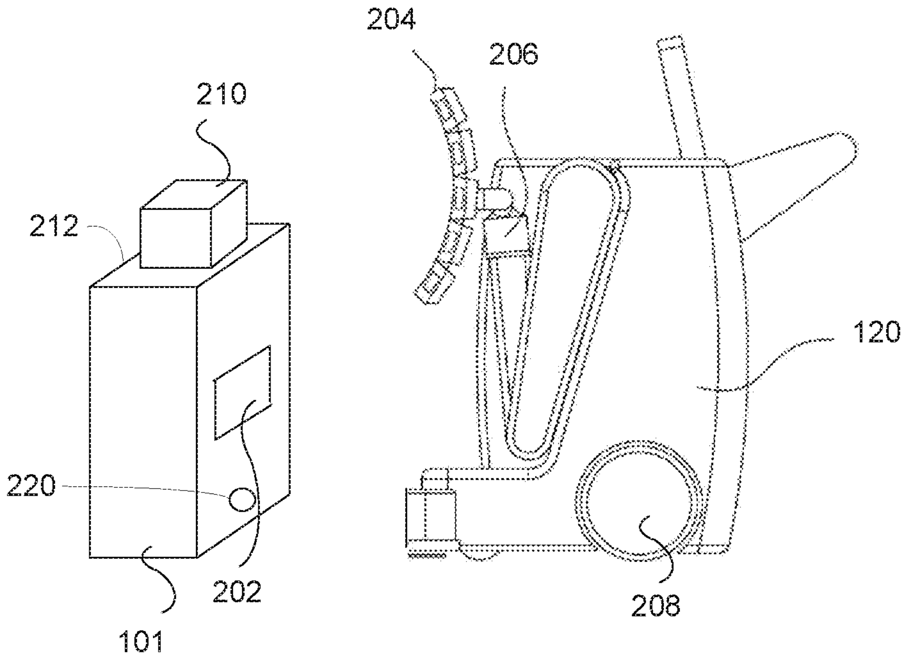
FIG. 2 depicts an exemplary configuration wherein a mobile imaging system is positioned at the station.

FIG. 2 depicts an exemplary configuration wherein an exemplary mobile imaging system 120 is positioned at the exemplary station 101. In some implementations, mobile imaging system 120 includes a detector (or gamma camera) 204 connected to, for example, an arm 206 via articulated coupling. Detector 204 may be a gamma ray detector that generates a tomographic image from a fixed position. Such gamma ray detector may be fabricated from semiconductor materials, such as cadmium zinc telluride (CdZnTe or CZT), cadmium telluride (CdTe), gallium arsenide (GaAs) and silicon (Si), among others. Detector 204 may be, for example, a SPECT detector that includes photomultiplier tubes or other photon detectors layered with a scintillation crystal. The photomultiplier tubes may be arranged along a rectangular or other grid to provide a two-dimensional planar array for detecting gamma radiation. Other types of detectors may be used.

Detector 204 may include a curved panel or a flat panel. When the mobile imaging system 120 is further away from a patient, medical image data with a larger field-of-view of the patient and lower resolution may be acquired. As the mobile imaging system 120 approaches the patient, medical image data of the patient with increasing resolution but decreasing field-of-view may be acquired. Image processing and/or reconstruction may be performed based on the acquired medical image data as the mobile imaging system 120 approaches the patient, allowing the mobile imaging system 120 to display tomographic images that "zoom" into the volume of interest.

Mobile imaging system 120 may move (e.g., autonomously, semi-autonomously, manually) and/or operate independently of the other mobile imaging systems. Mobile imaging system 120 may include a transport unit 208 to autonomously or semi-autonomously position the mobile imaging system 120 near the desired location (e.g., docking station, patient). In some implementations, the transport unit 208 includes at least one mobile structure (e.g., wheels, cylinders, rollers, legs) for freely moving the mobile imaging system 120, a drive module for driving the at least one mobile structure and a sensor module. The drive module may include a motor (e.g., electric motor) that may be driven by a human operator or self-driven in response to a signal. The sensor module includes one or more sensors for determining position and/or orientation of the mobile imaging system 120, detecting obstacles to avoid collisions, and/or detecting the position of the patient or station 101. The one or more sensors may include, for example, a camera, range sensor, ultrasound sensor, infrared sensor, global positioning sensor, or a combination thereof.

Mobile imaging system 120 may further include a battery (not shown), such as an auxiliary battery. The battery may be arranged at a side portion or a central portion of the mobile imaging system 120. The battery may be a separate battery which can be separated from the X mobile imaging system 120 or an integral type which is integrated with the mobile imaging system 120. The battery may be charged outside, while being separated from the mobile imaging system 120, or may be charged by wires via a terminal at station 101. Alternatively, the battery may be charged wirelessly.

Mobile imaging system 120 may autonomously move to the station 101 for charging, calibration, and/or other maintenance tasks. For example, mobile imaging system 120 may sense that its battery level is below a predetermined value (i.e., low) and move to the nearest station 101 for charging. Alternatively, station 101 may summon the mobile imaging system 120 to undergo calibration or other maintenance by sending out a wireless signal. This may be performed in accordance with a pre-defined schedule or in response to the occurrence of a pre-defined event. The mobile imaging system 120 may then move to the station 101 in response to the wireless signal. In other implementations, a technician may manually move the mobile imaging system 120 to the station 101 for performing maintenance tasks.

Station 101 may include a charging pad 202 for wirelessly charging mobile imaging system 120. The charging pad 202 may include an induction coil that generates an inducement current to wirelessly charge a battery in mobile imaging system (120*a* or 120) in close proximity. The induction coil may be configured to receive input power from an external power source, such as a standard wall power outlet. More than one charging pad 202 may also be provided. For example, one charging pad 202 may be provided for each of the four sides of the station 101 for charging multiple mobile imaging systems 120. Alternatively, multiple charging pads 202 may be provided for one or more sides of the station 101. Other configurations are also possible. Location of the charging pad 202 may vary according to the location of the battery in the mobile imaging system 120 to enable optimal charging. In some implementations, mobile imaging system 120 may include one or more charging terminals (not shown). The charging terminal may be physically and electrically coupled to a power supply connector at the station 101 for wired charging. Charging may be continuously performed while calibration of the mobile imaging system 120 is performed.

Station 101 may further include a calibration source container 210 for enclosing and/or supporting a calibration source. Calibration source container 210 may be mounted on an upper surface 212 of the station 101 for easy access of the calibration source. Alternatively, the calibration source container 210 is positioned within a recess (not shown) in the station 101. More than one calibration source containers 210 may be provided on station 101. A calibration source is positioned in each calibration source container 210.

Mobile imaging system 120 may be positioned at a predetermined distance from calibration source container 210. In some implementations, one or more sensors are provided to facilitate proper positioning of the mobile imaging system 120 for servicing. Such sensors may be provided on station 101 and/or mobile imaging system 120. Such sensors include, for example, proximity sensors (e.g., infrared, inductive, capacitive proximity sensors), camera-based sensors, ultrasound-based sensors, or a combination thereof. Other types of sensors may also be provided.

Figure 3A:
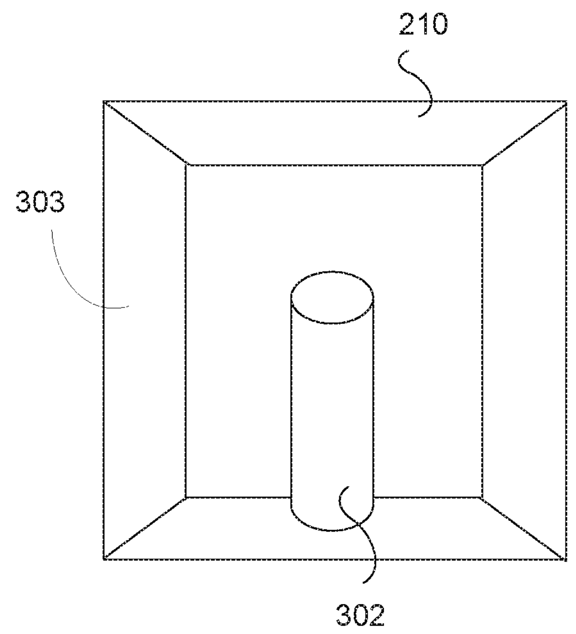
FIG. 3*a* shows an exemplary calibration source container.

FIG. 3*a* shows an exemplary calibration source container 210. Calibration source 302 is positioned in the calibration source container 210. Calibration source 302 may be an isotropic point source for measuring planar sensitivity. Alternatively, the calibration source is a sheet source for measuring uniformity. Other types of calibration sources may be used. The activity of the calibration source 302 should be adequate to enable the respective calibration. In some implementations, calibration source 302 is a long-lived, factory-calibrated radioisotope. The radioisotope of the calibration source 302 is long-lived relative to the radioisotope ingested by or used for emitting gamma rays from the patient. If the half-life of the radioisotope is long enough (e.g., greater than 2 months, 3 months, 6 months, 1 year, or more), then frequent replacement of the calibration source 302 is avoided.

Figure 3B:
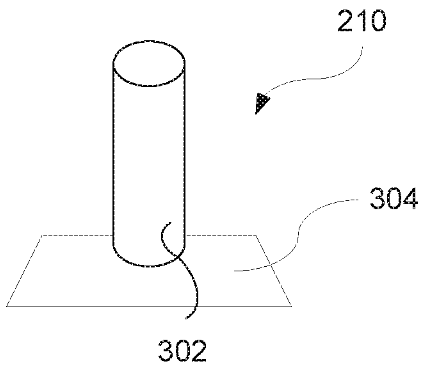
FIG. 3*b* shows another exemplary calibration source container.

In some implementations, calibration source container 210 is a box chamber with a pivoting or sliding door (or window) 303 for access. Alternatively, a pinhole opening may be provided. FIG. 3*b* shows another exemplary calibration source container 210. The calibration source container 210 includes a retractable platform 304 with no walls. The platform 304 with the calibration source 302 may be wholly retracted into a recess in the station 101 for storage. The platform 304 with the calibration source 302 may be raised to perform calibration.

Returning to FIG. 3*a*, calibration source container 210 is lined with a radiation shielding material to reduce and control radiation in the area surrounding the container 210 (e.g., reduce radiation exposure to personnel). The shielding material includes, for example, lead, tungsten, or other suitable material. Advantageously, the shielding material may be a particularly thick (and thus heavy) layer because station 101 is stationary and does not need to move. A thick shielding layer advantageously enables the use of a calibration source 302 with higher energies. For some calibration procedures, the nominal activity of calibration source may be increased to reduce the time to perform the procedure, as well as to minimize the frequency at which the source has to be renewed.

Figure 4:
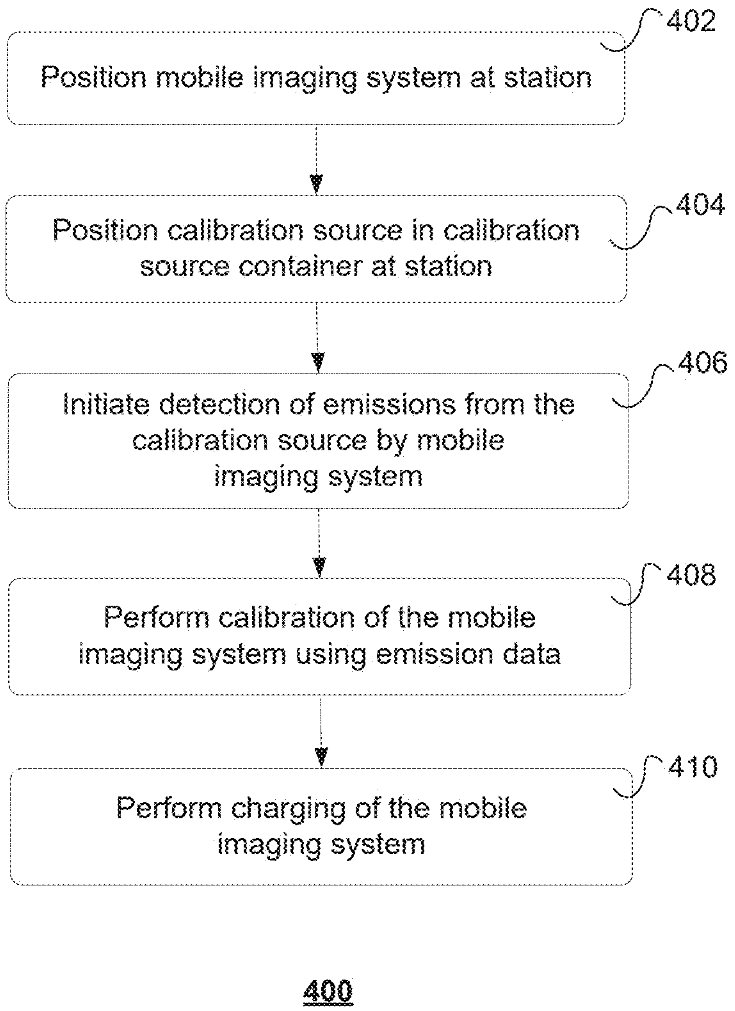
FIG. 4 shows an exemplary method of automated calibration and charging.

FIG. 4 shows an exemplary method 400 of automated calibration and charging. It should be understood that the steps of the method 400 may be performed in the order shown or a different order. Additional, different, or fewer steps may also be provided. Further, the method 400 may be implemented with at least one station 101 of FIGS. 1-3, a different system, or a combination thereof.

At 402, mobile imaging system 120 is positioned at station 101. In some implementations, mobile imaging system 120 autonomously moves to the station 101 for a maintenance task to be performed. Mobile imaging system 120 may autonomously move to the station 101 in response to, for example, receiving a signal sent out by station 101 to summon the mobile imaging system 120 or in response to the maintenance module 107 detecting occurrence of a predefined event. Such events may include, but are not limited to, battery level dropping below a predetermined value, scheduled maintenance time, user input, change in system software or hardware, or a combination thereof. Mobile imaging system 120 may also be manually moved to the station 101. Sensors (e.g., proximity sensors, camera-based sensors, ultrasound-based sensors) 220 may be provided either on the mobile imaging system 120 or the station 101 to ensure that mobile imaging system 120 is in the right location for receiving maintenance service. Mobile imaging system 120 may then initiate the station 101 to perform the maintenance task, such as charging or calibration.

Detector 204 of mobile imaging system 120 may be positioned at a predetermined distance (e.g., 20 cm) from calibration source 302. Detector 204 may be moved to the desired height and/or angular position by the articulating arm 206 to facilitate selective positioning with respect to calibration source 302. Detector 204 may include, for example, multiple cameras that can change from a flat panel configuration to a curved panel configuration (detector 310*b*) to optimize image acquisition. More than one mobile imaging system 120 may be positioned at the station 101. In some implementations, two or more mobile imaging systems (120*a*, 120*b*) are dispatched to two or more sides of the station 101.

At 404, a calibration source 302 is positioned in calibration source container 210 at the station 101. Calibration source 302 may be a long-lived factory-calibrated source. In some implementations, calibration source 302 generates gamma ray emissions at different known energies (e.g., energies at two or more levels). Multiple emission energy peaks may be used for calibration. Calibration source 302 may be formed with a mix of different isotopes. Each radiotracer causes emissions at a different energy, so the mix has one isotope emitting at one energy and another isotope emitting at another energy. More than two isotopes may also be used, providing a calibration source with peak energy emissions at three or more energies. Alternatively, a radionuclide with different emission energies may be used without being in a mix.

At 406, maintenance module 107 initiates detection of emissions from the calibration source 302 by the mobile imaging system 120 to generate emission data. Emissions from the calibration source 302 may be detected over time. Detector 204 of mobile imaging system 120 detects and converts the emissions into emission data. A collimator may be positioned in front of the detector 204 to limit the direction of photons detected by the detector 204, so each detected emission is associated with an energy and line or cone of possible locations from which the emission occurred. The lateral position of the line or cone relative to the detector 204 may likewise be determined.

Detector 204 detects the emissions and generates emission data. Emission data may include location data and energy data of the detected emission, as well as counts of detected gamma photons. The counts may be obtained for different energy or acquisition windows. For each energy level of the calibration source 302, a count of photons may be collected. Any size window or energy range may be used, such as 20% of the peak energy. Emissions within the energy window are included in the count. Counts are provided for each of two or more energy windows to count emissions from the same calibration source at a same time. The planar sensitivity and/or uniformity are energy dependent, so the separate counts for the separate energies are used to determine the planar sensitivity and/or uniformity for different energies.

At 408, maintenance module 107 performs calibration of mobile imaging system 120 using the emission data. In some implementations, maintenance module 107 performs calibration of the detector (or gamma camera) 204 of the mobile imaging system 120. Calibration may be performed by measuring the response to predetermined inputs and correcting the data acquired at the time of imaging to remove image non-uniformities caused by the detector 204. More particularly, maintenance module 107 may perform calibration by measuring and evaluating one or more performance parameters derived from the emission data, and determining corrections of acquired data based on such performance parameters. Performance parameters may include, but are not limited to, planar sensitivity, uniformity, spatial resolution, spatial linearity, energy, energy linearity, energy resolution, congruency, peaking, field-of-view, three-dimensional (3D) point of interaction, or a combination thereof. Other types of performance parameters are also useful. Maintenance module 107 may output the performance parameters to mobile imaging system 120. Additionally, maintenance module 107 may store a record of the performance parameters for each mobile imaging system 120 in a database.

In some implementations, detector 204 is calibrated as a function of the emissions at multiple energy levels of the calibration source 302. The calibration is for an emission energy of the radiotracer used with the patient, so a pool of available calibration sensitivities is used to find a closest emission energy, surrounding emission energies, or all of the emission energies of the calibration. Maintenance module 107 calibrates the detector 204 by, for example, measuring the sensitivities from the detector counts and a looked-up or known activity concentration of the calibration source 302. More particularly, maintenance module 107 may derive the planar sensitivity and/or uniformity for the emission energy of the radiotracer, at least in part, from the known set of planar sensitivities and/or uniformities measured with the calibration source 302.

In some implementations, planar sensitivity is determined by measuring the time from the first or initial count to a given number of counts. The sensitivity is the number of counts divided by the time and the dose of the calibration source 302. The dose or activity concentration of the calibration source 302 is known. Other calculations of sensitivity may also be used. The planar sensitivity is measured for two or more energies. The total number of counts per unit time (i.e., count rate) from the isotropic point source is measured at each energy. These count rates for the different energies are the same or different. The count rates are divided by the activity concentration of the calibration source 302, providing sensitivities as a function of energy. Planar sensitivity may be used in image reconstruction.

For uniformity, the sensitivity varies as a function of location on detector 204. Location-specific sensitivity is calculated from the location of specific counts. A sheet calibration source 302 emits uniformly (e.g., within a 10% tolerance) to each of the different locations on the planar detector 204. Maintenance module 107 calculates sensitivities at different locations on the detector 204. Different locations may have different sensitivities. A sensitivity at a reference location, an average sensitivity, or the planar sensitivity is used as a reference. Maintenance module 107 calculates a difference from the reference in the sensitivity at each location. Uniformity is determined as a collection of differences as a function of location. The differences are weights to be applied as a function of location to counts of emissions detected from a patient. Other measures of variance may also be used. Other representation of uniformity may also be used, such as a fit surface to the differences or the location-specific sensitivities themselves.

In some implementations, maintenance module 107 evaluates the performance parameters to perform quality control, so as to ensure that the performance parameters of the mobile imaging system 120 are within predefined acceptable ranges. If a performance parameter is out of tolerance or the predefined acceptable ranges, maintenance module 107 updates the corresponding correction table (e.g., uniformity or sensitivity correction). The correction table may be applied during image reconstruction to account for the nonuniformity caused by detector 204. A mobile imaging system 120 may be automatically flagged for failing quality control in response to the one or more performance parameters falling outside a predefined range.

In some implementations, cross-calibration is performed by comparing the performance parameters of the mobile imaging system 120 with the performance parameters of another mobile imaging system. Cross-calibration ensures that measurements are not only accurate but also comparable across different mobile imaging systems. In some implementations, steps 402 through 408 are repeated for multiple mobile imaging systems 120 to perform cross-calibration within a fleet. Each mobile imaging system 120 acquires emission data of the calibration source 302 under the same controlled conditions (e.g., same distance, same environmental factors). Any discrepancies in the performance parameters derived from the emission data may indicate a need for recalibration.

More particularly, the emission data may be analyzed by, for example, maintenance module 107, to determine, for example, the camera's response to the known quantity of radioactivity (e.g., measured in counts per unit activity) or other performance parameters. Maintenance module 107 may compare the performance parameters of different mobile imaging systems, wherein the performance parameters are derived from different sets of emission data acquired by the different mobile imaging systems from the same calibration source 302. Any discrepancies in the performance parameters may indicate a need for recalibration. Adjustments may be made to the settings (e.g., energy window settings, detector sensitivity adjustments) of the mobile imaging systems 120 to align the measurements with those of a reference standard or with each other. After adjustments are made, additional sets of emission data may be acquired by the different mobile imaging systems from the calibration source 302 to verify that the performance parameters match or are within acceptable tolerances. Cross-validation thus ensures that the different mobile imaging systems 120 provide uniform results, which is critical for consistent patient diagnosis and treatment.

At 410, charging of mobile imaging system 120 is performed. Charging may occur concurrently with calibration of mobile imaging system 120 (i.e., steps 404, 406 and/or 408). In some implementations, charging is wirelessly performed using the charging pad 202. Once the mobile imaging system 120 is positioned at station 101, maintenance module 107 may activate an induction coil within the charging pad 202 and provide energy to charge one or more batteries in mobile imaging system 120.

In some implementations, charging is performed via wired connections to mobile imaging system 120. For example, mobile imaging system 120 may include one or more charging terminals that are physically engaged with one or more power supply connectors at station 101 when the mobile imaging system 120 is docked at the station 101. Charging may begin automatically when the one or more batteries of mobile imaging system 120 are electrically coupled to the power supply connector at station 101.

During the charging operation, the battery control circuits in mobile imaging system 120 may monitor the state of charge of the battery, and may instruct the station 101 to terminate charging when a pre-determined charge-state is reached. For example, charging may terminate when the battery reaches a full state of charge.

The following is a list of non-limiting illustrative embodiments disclosed herein:

Illustrative embodiment 1. A calibration station, comprising: at least one charging unit that supplies power to charge a mobile imaging system; a calibration source; a non-transitory memory device for storing computer readable program code; and a processor device in communication with the non-transitory memory device, the processor device being operative with the computer readable program code to perform steps including: initiating detection of emissions from the calibration source by the mobile imaging system to generate emission data, and performing calibration of the mobile imaging system using the emission data.

Illustrative embodiment 2. The calibration station of illustrative embodiment 1 wherein the mobile imaging system comprises a gamma ray detector.

Illustrative embodiment 3. The calibration station of any one of illustrative embodiments 1-2 wherein the charging unit comprises one or more charging pads for wireless charging.

Illustrative embodiment 4. The calibration station of any one of illustrative embodiments 1-3 further comprises one or more sensors that facilitate positioning of the mobile imaging system.

Illustrative embodiment 5. The calibration station of any one of illustrative embodiments 1-4 further comprises a calibration source container for enclosing or supporting the calibration source.

Illustrative embodiment 6. The calibration station of illustrative embodiment 5 wherein the calibration source container is mounted on an upper surface of the station.

Illustrative embodiment 7. The calibration station of illustrative embodiment 5 wherein the calibration source container comprises a box chamber with a pivoting or sliding door for access.

Illustrative embodiment 8. The calibration station of illustrative embodiment 5 wherein the calibration source container comprises a retractable platform.

Illustrative embodiment 9. The calibration station of illustrative embodiment 5 wherein the calibration source container is lined with a radiation shielding material.

Illustrative embodiment 10. A calibration method, comprising: positioning a first mobile imaging system at a station; initiating detection, by the first mobile imaging system, of emissions from a calibration source at the station to generate emission data; and performing calibration of the first mobile imaging system using the emission data.

Illustrative embodiment 11. The calibration method of illustrative embodiment 10 wherein positioning the first mobile imaging system at the station comprises autonomously moving the first mobile imaging system in response to a signal received from the station.

Illustrative embodiment 12. The calibration method of any one of illustrative embodiments 10-11 wherein positioning the first mobile imaging system at the station comprises autonomously moving the first mobile imaging system in response to detecting a predefined event.

Illustrative embodiment 13. The calibration method of any one of illustrative embodiments 10-12 wherein positioning the first mobile imaging system at the station comprises positioning a detector of the first mobile imaging system at a predetermined distance from the calibration source.

Illustrative embodiment 14. The calibration method of any one of illustrative embodiments 10-13 wherein performing calibration of the first mobile imaging system comprises measuring one or more performance parameters and determining one or more corrections based on the one or more performance parameters.

Illustrative embodiment 15. The calibration method of illustrative embodiment 14 wherein the one or more performance parameters comprise planar sensitivity, uniformity, spatial resolution, spatial linearity, energy, energy linearity, energy resolution, congruency, peaking, field-of-view, three-dimensional (3D) point of interaction, or a combination thereof.

Illustrative embodiment 16. The calibration method of illustrative embodiment 14 further comprises flagging the first mobile imaging system for failing quality control in response to the one or more performance parameters falling outside a predefined range.

Illustrative embodiment 17. The calibration method of any one of illustrative embodiments 10-16 wherein performing the calibration of the first mobile imaging system comprises performing cross-calibration of the first mobile imaging system with a second mobile imaging system.

Illustrative embodiment 18. The calibration method of any one of illustrative embodiments 10-17 further comprising charging the first mobile imaging system at the station.

Illustrative embodiment 19. The calibration method of illustrative embodiment 18 wherein charging the first mobile imaging system is performed concurrently with performing the calibration of the first mobile imaging system.

Illustrative embodiment 20. One or more non-transitory computer-readable media embodying instructions executable by machine to perform operations, comprising: positioning a mobile imaging system at a station; initiating detection, by the mobile imaging system, of emissions from a calibration source at the station to generate emission data; and performing calibration of the mobile imaging system using the emission data.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A calibration station, comprising:

at least one charging circuitry that supplies power to charge a mobile imaging system;

a calibration source;

a non-transitory memory device for storing a computer readable program code; and a processor device in communication with the non-transitory memory device, the processor device being operative with the computer readable program code to perform steps including:

initiating a detection of emissions from the calibration source by the mobile imaging system to generate emission data, and performing a calibration of the mobile imaging system using the emission data.

2. The calibration station of claim 1 wherein the mobile imaging system comprises a gamma ray detector.

3. The calibration station of claim 1 wherein the at least one charging circuitry comprises one or more charging pads for wireless charging the mobile imaging system.

4. The calibration station of claim 1 further comprising one or more sensors that facilitate positioning of the mobile imaging system.

5. The calibration station of claim 1 further comprising a calibration source container for enclosing or supporting the calibration source.

6. The calibration station of claim 5 wherein the calibration source container is mounted on an upper surface of the calibration station.

7. The calibration station of claim 5 wherein the calibration source container comprises a box chamber with a pivoting door or a sliding door for access.

8. The calibration station of claim 5 wherein the calibration source container comprises a retractable platform.

9. The calibration station of claim 5 wherein the calibration source container is lined with a radiation shielding material.

10. A calibration method, comprising:

positioning a first mobile imaging system at a station;

initiating a detection, by the first mobile imaging system, of emissions from a calibration source at the station to generate emission data; and performing a calibration of the first mobile imaging system using the emission data.

11. The calibration method of claim 10 wherein positioning the first mobile imaging system at the station comprises autonomously moving the first mobile imaging system in response to a signal received from the station.

12. The calibration method of claim 10 wherein positioning the first mobile imaging system at the station comprises autonomously moving the first mobile imaging system in response to detecting a predefined event.

13. The calibration method of claim 10 wherein positioning the first mobile imaging system at the station comprises positioning a detector of the first mobile imaging system at a predetermined distance from the calibration source.

14. The calibration method of claim 10 wherein performing the calibration of the first mobile imaging system using the emission data comprises measuring one or more performance parameters and determining one or more corrections based on the one or more performance parameters.

15. The calibration method of claim 14 wherein the one or more performance parameters comprise a planar sensitivity, a uniformity, a spatial resolution, a spatial linearity, an energy, an energy linearity, an energy resolution, a congruency, a peaking, a field-of-view, a three-dimensional (3D) point of interaction, or a combination thereof.

16. The calibration method of claim 14 further comprising flagging the first mobile imaging system for failing a quality control in response to the one or more performance parameters falling outside a predefined range.

17. The calibration method of claim 10 wherein performing the calibration of the first mobile imaging system using the emission data comprises performing a cross-calibration of the first mobile imaging system with a second mobile imaging system.

18. The calibration method of claim 10 further comprising charging the first mobile imaging system at the station.

19. The calibration method of claim 18 wherein charging the first mobile imaging system at the station is performed concurrently with performing the calibration of the first mobile imaging system using the emission data.

20. One or more non-transitory computer-readable media embodying instructions executable by a machine to perform operations, comprising:

positioning a mobile imaging system at a station;

initiating a detection, by the mobile imaging system, of emissions from a calibration source at the station to generate emission data; and performing a calibration of the mobile imaging system using the emission data.

* * * * *